(12) United States Patent
Tai et al.

(10) Patent No.: US 9,781,842 B2
(45) Date of Patent: Oct. 3, 2017

(54) LONG-TERM PACKAGING FOR THE PROTECTION OF IMPLANT ELECTRONICS

(71) Applicant: California Institute of Technology, Pasadena, CA (US)

(72) Inventors: Yu-Chong Tai, Pasadena, CA (US); Han-Chieh Chang, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 352 days.

(21) Appl. No.: 14/142,180

(22) Filed: Dec. 27, 2013

(65) Prior Publication Data
US 2015/0036302 A1 Feb. 5, 2015

Related U.S. Application Data

(60) Provisional application No. 61/862,180, filed on Aug. 5, 2013.

(51) Int. Cl.
*H01G 2/12* (2006.01)
*H05K 3/40* (2006.01)
(Continued)

(52) U.S. Cl.
CPC ....... *H05K 3/4038* (2013.01); *H01L 23/3135* (2013.01); *H05K 3/284* (2013.01); *A61F 9/0017* (2013.01); *H01L 2224/73204* (2013.01); *H01L 2924/0002* (2013.01); *H05K 1/032* (2013.01); *H05K 3/0041* (2013.01); *H05K 3/281* (2013.01); *H05K 3/282* (2013.01); *H05K 3/285* (2013.01); *H05K 3/381* (2013.01); *H05K 2201/017* (2013.01); *H05K 2201/1003* (2013.01); *H05K 2201/10015* (2013.01);
(Continued)

(58) Field of Classification Search
CPC ....................................................... H01G 2/12
USPC ....................................................... 174/524
See application file for complete search history.

(56) References Cited

U.S. PATENT DOCUMENTS 777,493 A 12/1904 Burke
5,178,957 A 1/1993 Kolpe et al.
(Continued)

FOREIGN PATENT DOCUMENTS

CN 101398614 4/2009
CN 101398614 A 4/2009
(Continued)

OTHER PUBLICATIONS

Ziaie, Babak et al., A hermetic glass-silicon micropackage with high-density on-chip feedthroughs for sensors and actuators, Journal of Microelectromechanical Systems, Sep. 1996, vol. 5, No. 3, pp. 166-179.
(Continued)

*Primary Examiner* — Timothy Thompson
*Assistant Examiner* — Stanley Tso
(74) *Attorney, Agent, or Firm* — Kilpatrick Townsend & Stockton LLP

(57) ABSTRACT

The present invention provides a micropackaged device comprising: a substrate for securing a device; a corrosion barrier affixed to said substrate; optionally at least one feedthrough disposed in said substrate to permit at least one input and or at least one output line into said micropackaged device; and an encapsulation material layer configured to encapsulate the micropackaged device.

23 Claims, 13 Drawing Sheets

(51) Int. Cl.
*H01L 23/31* (2006.01)
*A61F 9/00* (2006.01)
*H05K 1/03* (2006.01)
*H05K 3/00* (2006.01)
*H05K 3/28* (2006.01)
*H05K 3/38* (2006.01)

(52) U.S. Cl.
CPC ......... *H05K 2201/10022* (2013.01); *H05K 2201/10075* (2013.01); *H05K 2201/10083* (2013.01); *H05K 2201/10287* (2013.01); *H05K 2201/10356* (2013.01); *H05K 2203/0139* (2013.01); *H05K 2203/0514* (2013.01); *H05K 2203/1316* (2013.01); *H05K 2203/1322* (2013.01); *H05K 2203/1338* (2013.01); *Y10T 29/49165* (2015.01)

(56) References Cited

U.S. PATENT DOCUMENTS

| | | | |
|---|---|---|---|
| 6,516,808 B2 * | 2/2003 | Schulman | A61B 5/14532 128/899 |
| 7,127,286 B2 | 10/2006 | Mech et al. | |
| 7,211,103 B2 | 5/2007 | Greenberg et al. | |
| 7,326,649 B2 | 2/2008 | Rodger et al. | |
| 7,494,749 B2 | 2/2009 | Haines et al. | |
| 7,774,931 B2 | 8/2010 | Tai et al. | |
| 7,807,211 B2 * | 10/2010 | Hossainy | A61F 2/82 427/2.1 |
| 8,133,698 B2 | 3/2012 | Silver et al. | |
| 8,423,143 B2 | 4/2013 | Bartic et al. | |
| 2002/0076528 A1 | 6/2002 | Tomsia et al. | |
| 2003/0233133 A1 | 12/2003 | Greenberg et al. | |
| 2004/0106262 A1 | 6/2004 | Theiss et al. | |
| 2004/0199235 A1 | 10/2004 | Younis et al. | |
| 2005/0147898 A1 | 7/2005 | Haines | |
| 2005/0268722 A1 | 12/2005 | Tai et al. | |
| 2006/0003090 A1 | 1/2006 | Rodger et al. | |
| 2006/0121639 A1 | 6/2006 | Tai et al. | |
| 2006/0138657 A1 | 6/2006 | Kushima et al. | |
| 2006/0184245 A1 * | 8/2006 | Graf | A61N 1/36046 623/6.63 |
| 2006/0247664 A1 | 11/2006 | Meng et al. | |
| 2007/0096281 A1 | 5/2007 | Greenberg et al. | |
| 2007/0293749 A1 | 12/2007 | Zhou | |
| 2008/0039792 A1 | 2/2008 | Meng et al. | |
| 2008/0058632 A1 | 3/2008 | Tai et al. | |
| 2008/0058895 A1 | 3/2008 | Ok et al. | |
| 2009/0198293 A1 | 8/2009 | Cauller et al. | |
| 2009/0228086 A1 | 9/2009 | Greenberg | |
| 2010/0041971 A1 | 2/2010 | Goode, Jr. et al. | |
| 2010/0265680 A1 * | 10/2010 | Tai | A61B 5/0031 361/760 |
| 2010/0294041 A1 | 11/2010 | Tai et al. | |
| 2010/0305550 A1 | 12/2010 | Meng et al. | |
| 2011/0021943 A1 * | 1/2011 | Lacour | A61N 1/0551 600/546 |
| 2011/0254171 A1 | 10/2011 | Guo et al. | |
| 2012/0009159 A1 | 1/2012 | Humayun et al. | |
| 2012/0289883 A1 | 11/2012 | Meng et al. | |
| 2012/0296423 A1 | 11/2012 | Caffey et al. | |
| 2012/0303118 A1 | 11/2012 | DeBoer et al. | |
| 2013/0000119 A1 | 1/2013 | Tai et al. | |
| 2013/0004560 A1 | 1/2013 | Ho et al. | |
| 2013/0137958 A1 | 5/2013 | Tai et al. | |
| 2013/0143326 A1 | 6/2013 | Tai et al. | |
| 2013/0144399 A1 | 6/2013 | Tai et al. | |
| 2013/0245412 A1 * | 9/2013 | Rong | A61B 5/14532 600/347 |
| 2013/0277846 A1 * | 10/2013 | Ziegler | H01L 24/27 257/769 |
| 2013/0297019 A1 | 11/2013 | Tai et al. | |
| 2014/0046439 A1 * | 2/2014 | Dos Santos | A61B 3/16 623/6.22 |
| 2015/0371929 A1 | 12/2015 | Tai et al. | |

FOREIGN PATENT DOCUMENTS

| | | |
|---|---|---|
| CN | 102355854 | 2/2012 |
| WO | 2002100769 A2 | 12/2002 |
| WO | 2010090706 A2 | 8/2010 |
| WO | 2015041944 A1 | 3/2015 |

OTHER PUBLICATIONS

Weiland, James, D, et al., A comparison of retinal prosthesis electrode array substrate materials, Proceedings of the 2009 Annual International Conference of the IEEE on Engineering in Medicine and Biology Society (EMBS), pp. 4140-4143.

Xie, Xianzong et al., Long-term bi-layer encapsulation performance of atomic layer deposited A1203 and Parylene C for biomedical implantable devices, IEEE Transactions on Biomedical Engineering, Jun. 6, 2013 (E-pub.), vol. 60, No. 10, pp. 2943-2951.

Chang, Jay Han-Chieh et al., Long term glass-encapsulated packaging for implant electronics, Proceedings of the 2014 IEEE 27$^{th}$ International Conference on Micro Electro Mechanical Systems (MEMS), Jan. 2014, pp. 1127-1130.

Chang et al., High yield pacakging for high-density multi-channel chip integration on 4 flexible parylene substrate. Micro Electro Mechanical Systems (MEMS), 2012 IEEE 25$^{th}$ Conference, pp. 353-356.

Rodger, Damien et al., Scalable high lead-count parylene package for retinal prostheses, Sensors and Actuators B117 (2006), vol. 117, Issue 1, 107-114.

Chang et al., High Density 256-Channel Chip Integration with Flexible Parylene Pocket, Solid State Sensors, Actuators and Microsystems Conference (Transducers), 2011 16$^{th}$ International Conference; pp. 378-381.

International Search Report, PCT/US2014/031759 mailing date Aug. 21, 2014, 3 pages.

Rodger et al., "Scalable high lead-count parylene package for retinal prostheses," Sensors and Actuators B, 2006, vol. 117, pp. 107-114.

Jay Han-Chieh Chang et al., "High Density 256-Channel Chip Integration with Flexible Parylene Pocket," Solid-State Sensors, Actuators and Microsystems Conference (TRANSDUCERS), 2011 16th International , pp. 378,381, Jun. 5-9, 2011.

Jay Han-Chieh Chang et al., "High Yield Packaging for High-Density Multi-Channel Chip Integration on Flexible Parylene Substrate," Micro Electro Mechanical Systems (MEMS), 2012 IEEE 25th International Conference on , pp. 353,356; Jan. 29, 2012-Feb. 2, 2012.

Jay Han-Chieh Chang et al., "Long Term Glass-Encapsulated Packaging for Implant Electronics," Proceeding of the 27th International Conference on Micro Electro Mechanical Systems, Jan. 26-30, 2014.

Jay Han-Chieh Chang et al., "A Low-Temperature Parylene-C-To-Silicon Bonding Using Photo-Patternable Adhesives and Its Applications," Proceeding of the 17th International Conference on Solid-State Sensors, Actuators and Microsystems, pp. 2217-2220, 2013.

Jay Han-Chieh Chang et al., "Reliable Packaging for Parylene-Based Flexible Retinal Implant," Proceeding of the 17th International Conference on Solid-State Sensors, Actuators and Microsystems, pp. 2612-2615, 2013.

International Search Report for corresponding PCT application PCT/US2013/031752 mailed Jun. 28, 2013.

International Search Report for corresponding PCT application PCT/US2016/049034 mailed Nov. 4, 2016 (7 pages).

Chang et al., "High density 256-channel chip integration with flexible parylene pocket", IEEE, 16th International Solid-State Sensors, Actuators and Microsystems Conference, Jun. 5-9, 2011, pp. 378-381.

Chang et al., "High yield packaging for high-density multi-channel chip integration on flexible parylene substrate", IEEE 25th International Conference on, Micro Electro Mechanical Systems, Jan. 29-Feb. 2, 2012, pp. 353-356.

Rodger et al., "Scalable High Lead-Count Parylene Package for Retinal Prostheses", Sensors and Actuators B, vol. 117, Issue 1, Sep. 12, 2006, pp. 107-114.

(56) References Cited

OTHER PUBLICATIONS

Supplementary European Search Report mailed Feb. 17, 2017 in European Patent Application No. 14834336.1, 9 pages.

* cited by examiner

*FIG. 6A*      *FIG. 6B*      *FIG. 6C*
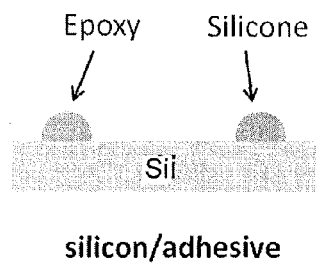
silicon/adhesive
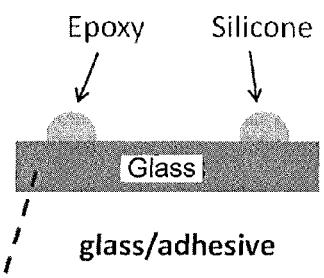
glass/adhesive
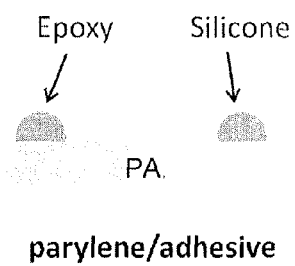
parylene/adhesive
*FIG. 6D*
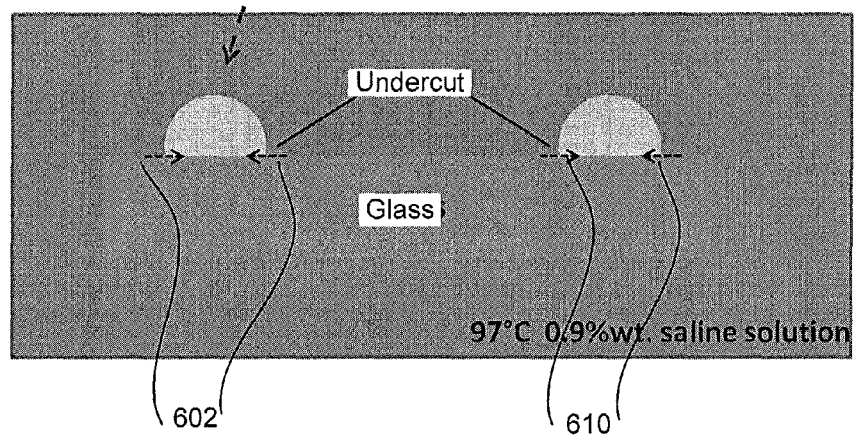

| Si substrate | | |
|---|---|---|
| UNDERCUT (μm/day) | N | SAP |
| Epoxy (M-121HP) | 31.2 | 4.8 |
| Silicone (MED-6219) | 12.5 | 2.2 |
| Glass substrate | | |
| UNDERCUT (μm/day) | N | SAP |
| Epoxy (M-121HP) | 17.4 | 4.9 |
| Silicone (MED-6219) | 13.3 | 2.9 |
| PA substrate | | |
| UNDERCUT (μm/day) | N | SAP |
| Epoxy (M-121HP) | 19.4 | 3.8 |
| Silicone (MED-6219) | 22.3 | 3.2 |

N: No Treatment ; SAP: Silicone Adhesion Promoter (MED-160)

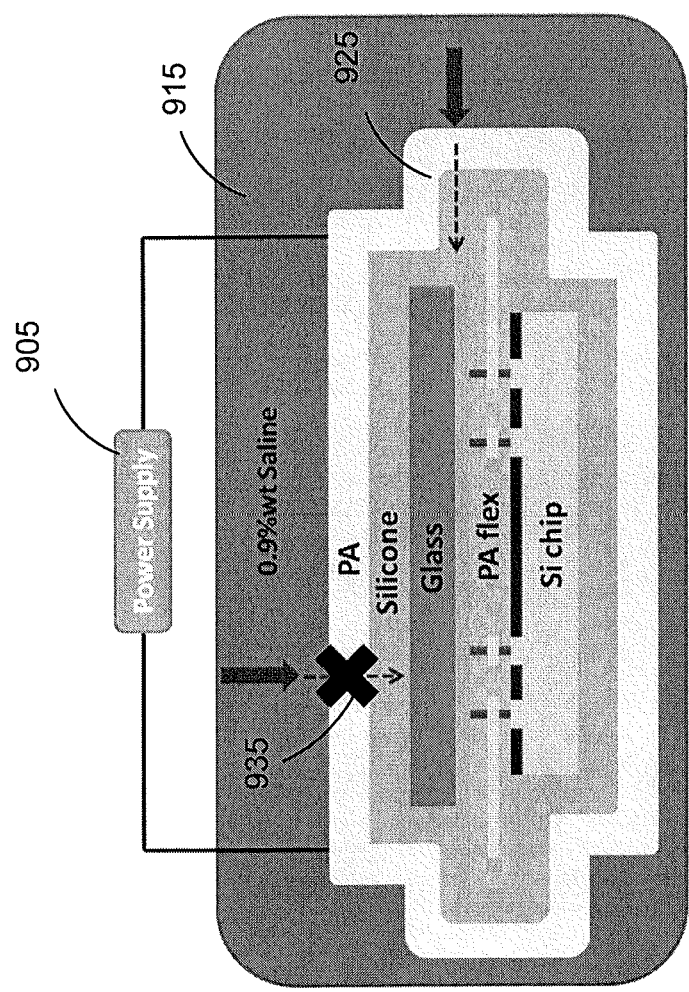
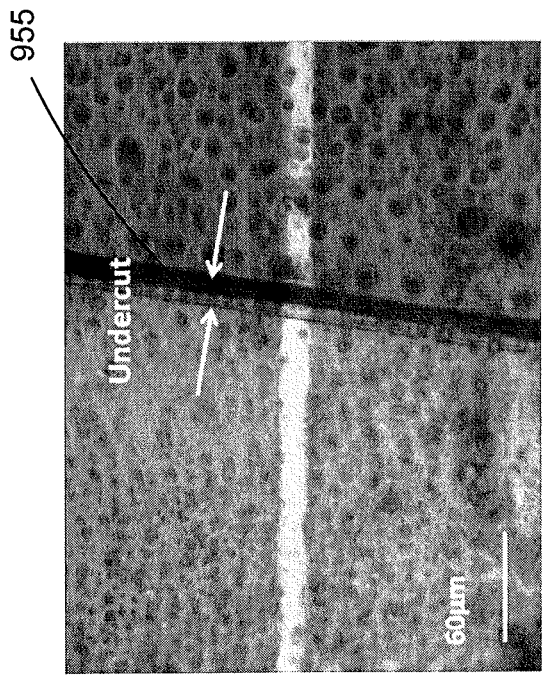
FIG. 9A
FIG. 9B

A: No protection; B: 40μm PA; C: 5mm silicone + 40μm PA ;
D: 40μm PA+5mm silicone+glass

| Protection | 97°C (day) | 87°C (day) | Ea(eV) | 37°C (day) |
|---|---|---|---|---|
| A | 1.7 | 2.6 | -0.40 | 20 days |
| B | 15 | 31 | -0.69 | 2.7 years |
| C | 40 | 82 | -0.68 | 6.9 years |
| D | 59 | 107 | -0.68 | 10.3 years |

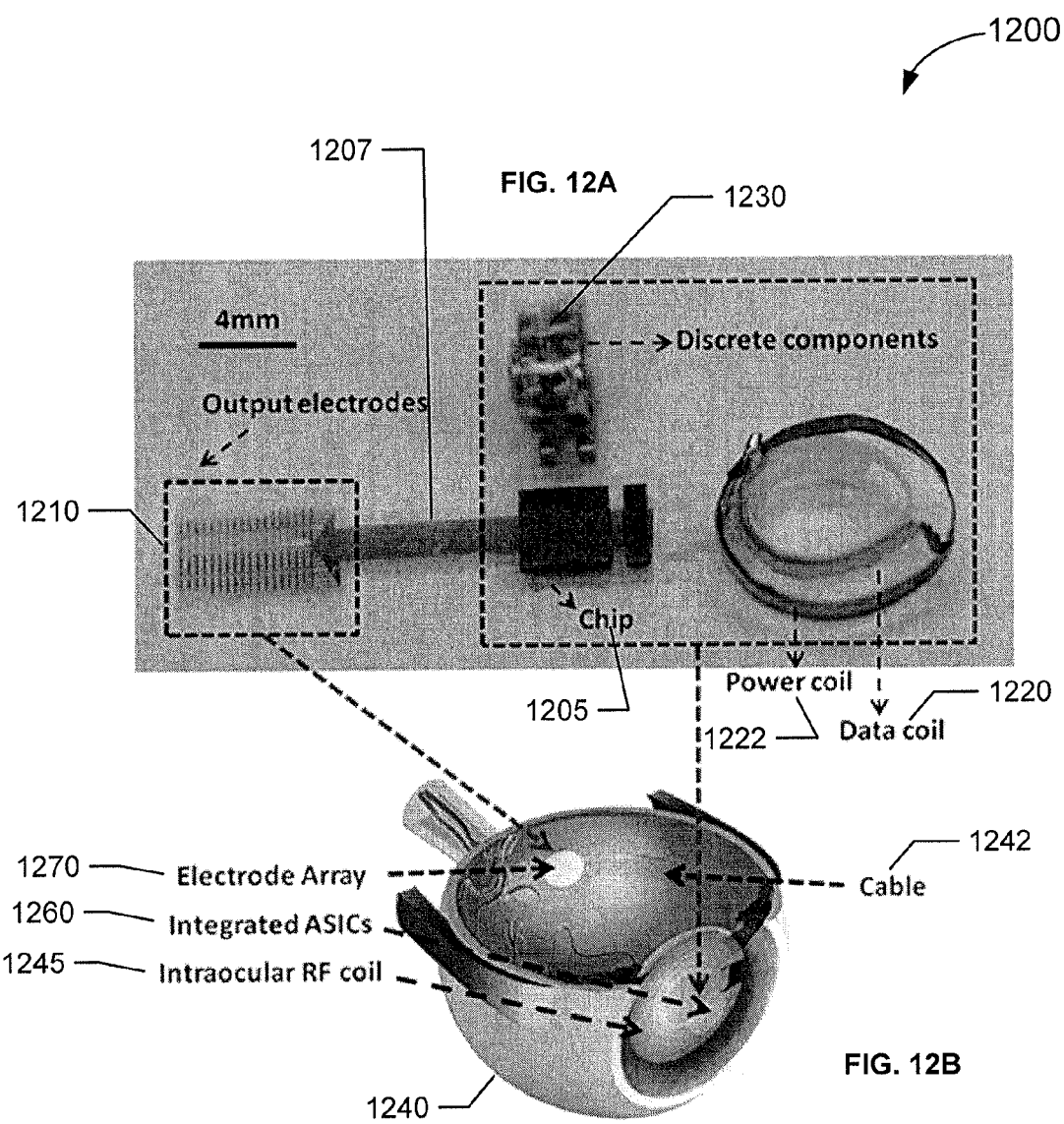

FIG. 13A  
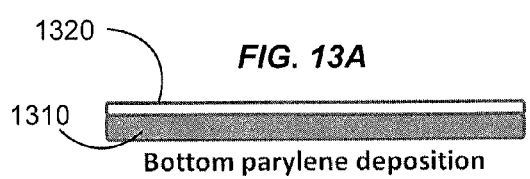
Bottom parylene deposition
FIG. 13B  
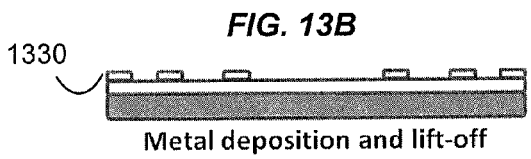
Metal deposition and lift-off
FIG. 13C  
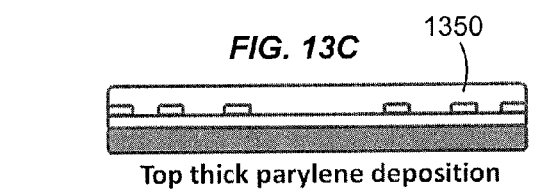
Top thick parylene deposition
FIG. 13D  
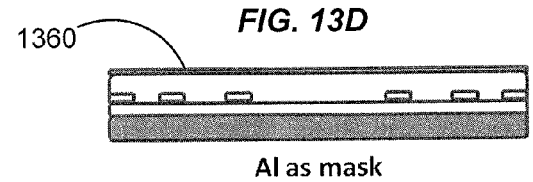
Al as mask
FIG. 13E  
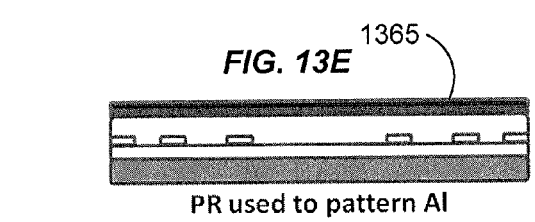
PR used to pattern Al
FIG. 13F  
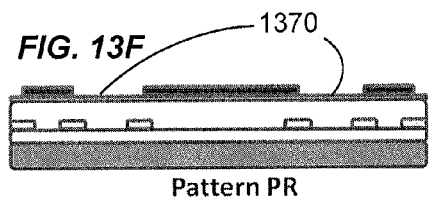
Pattern PR
FIG. 13G  
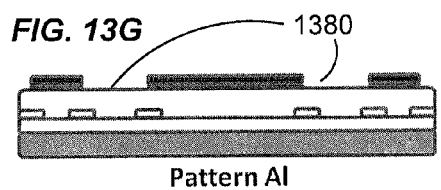
Pattern Al
FIG. 13H  
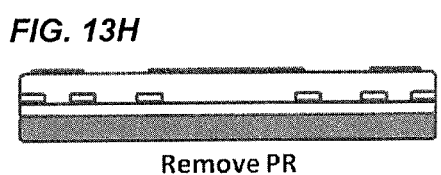
Remove PR
FIG. 13I  
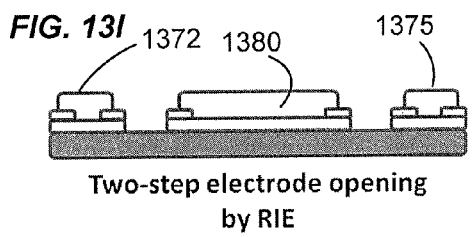
Two-step electrode opening by RIE
FIG. 13J  
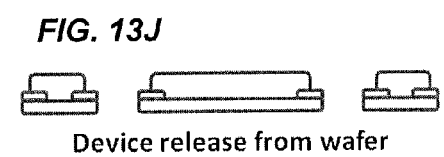
Device release from wafer
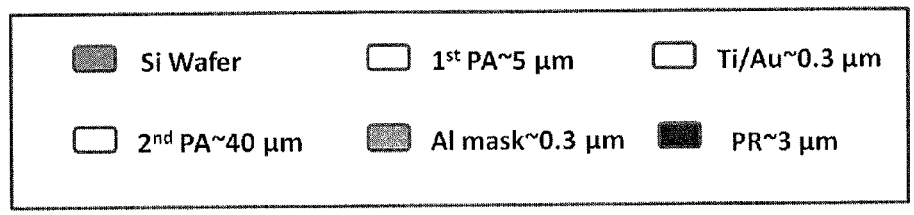
Legend: Si Wafer; 1st PA~5 μm; Ti/Au~0.3 μm; 2nd PA~40 μm; Al mask~0.3 μm; PR~3 μm

LONG-TERM PACKAGING FOR THE PROTECTION OF IMPLANT ELECTRONICS

CROSS-REFERENCES TO RELATED APPLICATIONS

This application claims priority to U.S. Patent Application No. 61/862,180, filed Aug. 5, 2013, which is incorporated herein by reference for all purposes.

STATEMENT AS TO RIGHTS TO INVENTIONS MADE UNDER FEDERALLY SPONSORED RESEARCH AND DEVELOPMENT

This invention was made with government support under EEC-0310723 awarded by the National Science Foundation. The government has certain rights in the invention.

BACKGROUND OF THE INVENTION

Biocompatible silicones have been used as encapsulation layers for decades but it is known that most silicones tend to have a rather large water vapor transmission rate (WVTR) due to their porous structure. One way to reduce the WVTR by adding another parylene-C coating on silicone is reported to seal the silicone layer and have very good adhesion to it (see, S. Sawano et al., *Digest Tech. Papers MEMS'08 Conference*, Tucson, USA, Jan. 13-17, 2008, pp. 419-422). However, the parylene-C coated bio-compatible silicone layer tends to be thick and can lose its elastic flexibility.

On the other hand, parylene-C has been extensively used in biomedical devices and interfaces as a structural material or a conformal and bio-compatible coating (see, J. H. Chang, R. Huang, Y. C. Tai, *Digest Tech. Papers Transducers '11 Conference*, Peking, Jun. 5-9, 2011, pp. 378-381). It has also become a packaging material because of its many favorable properties (see, J. H. Chang, D. Kang, Y. C. Tai, *Digest Tech. Papers MEMS'12 Conference*, Paris, Jan. 29-Feb. 2, 2012, pp. 353-356). The water permeability and the chemical stability of parylene-C have also been studied (see, Y. Hu et al., *Journal of Applied Polymer Science*, vol. 81, pp. 1624-1633, 2000; W. Li et al., *ECS Transactions*, vol. 11, pp. 1-6, 2008), and the results show that parylene-C is a very good bioinert insulator and parylene-C protected electrodes can survive a sufficiently long time with metals sandwiched by 9.2 μm parylene-C on each side.

One of the biggest challenges that a prosthetic implant has to overcome is the reliable packaging of integrated circuit (IC) chips so that bio-devices can withstand corrosive body fluids. What is needed in the art is a complete wireless retinal implant with high density multi-channel IC chips, discrete components (caps, inductors, and oscillators), and coils (power and data coils) packaged with a high-density stimulating electrode array. Appropriate packaging of the retinal implant in a mammalian body to achieve a long lifetime is also needed. The present invention satisfies these and other needs.

BRIEF SUMMARY OF THE INVENTION

In one embodiment, the present invention provides a micropackaged device, the device comprising:
 a substrate for securing a device;
 a corrosion barrier affixed to the substrate;
 optionally at least one feedthrough disposed in the substrate to permit at least one input and or at least one output line into the micropackaged device; and
 an encapsulation material layer configured to encapsulate the micropackaged device.

In certain aspects, the present invention provides a micropackaged device comprising a substrate such as a thin film substrate. In certain aspects, the thin-film substrate comprises:
 a first thin-film layer;
 a metal adjacent to the first thin-film layer; and
 a second thin-film layer adjacent to the metal to form a thin-film metal thin-film sandwich (thin-film/metal/thin-film), wherein the second layer of thin-film has an opening, the opening having at least one electrical contact provided on an internal surface thereof, the opening configured to accept at least one electrical circuit device and to provide electrical communication between the at least one electrical contact and the at least one electrical circuit device.

In another embodiment, the present invention provides a method for micropackaging a device, the method comprising:
 providing a substrate for securing a device;
 affixing a corrosion barrier to the substrate;
 optionally providing at least one feedthrough disposed in the substrate to permit at least one input and or at least one output line into the micropackaged device; and
 encapsulating the micropackaged device.

In one embodiment, the present invention provides a protective architecture such as a corrosion barrier in conjunction with an encapsulation layer. In certain aspects, the corrosion barrier decreases the water vapor transmission rate (WVTR) even further than the encapsulation layer alone. The WVTR is one parameter that can aid in quantifying the effectiveness of an encapsulation layer(s) and/or a corrosion protection barrier.

In certain aspects, the present invention provides an encapsulating material layer together with a corrosion barrier to protect a micropackaged device or an implant from corrosive bodily fluid. The corrosion barrier can be a low-permeation material such as glass, metal such as a thin metal film, ceramic, parylene, silicone, PET, PVC or a combination thereof, which affords the implant even further protection over the encapsulation layer alone.

These and other aspects, objects and embodiments will become more apparent when read with the following detailed description and figures which follow.

BRIEF DESCRIPTION OF THE DRAWINGS

FIGS. 6A-D show certain of the interfaces in the micropackaging schemes of the present invention.

FIGS. 9A-B show (A) one embodiment of a testing sample with a glass-encapsulated packaging under an active soaking test; (B) shows an embodiment with a very slow undercut along the interface as the main failure.

FIGS. 12A-B illustrate (A) a schematic representation of the retinal implant connected with IC chips, coils, and discrete components; (B) shows implantation into a mammalian eye.

FIGS. 13A-J show one embodiment of a fabrication process of a substrate structure of the present invention; (A) shows a parylene-C layer on a silicon substrate; (B) shows metal deposition and lift-off; (C) shows a second parylene deposition; (D) shows a metal as a mask; (E) shows photoresist being used as a pattern; (F) shows a patterned photoresist layer; (G) shows patterned metal layer; (H) shows removal of the photoresist; (I) shows a two-step electrode opening; and (J) shows the silicon wafer is released.

DETAILED DESCRIPTION OF THE INVENTION

I. Embodiments

Figure 1:
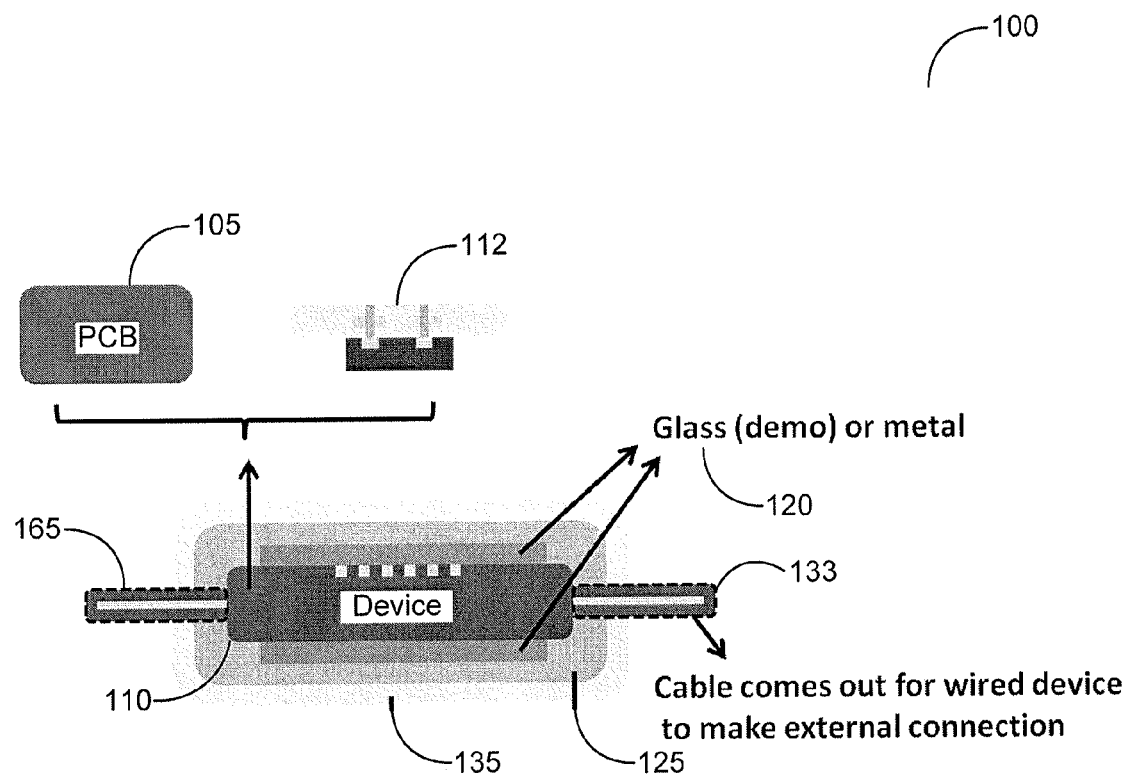
FIG. 1 shows one embodiment of a micropackaged device of the present invention.

Aspects of the present invention are directed to a micropackaged electronic device(s) and/or component(s) for use as an implantable medical device. In some aspects, the electronics are hermetically sealed within a biocompatible housing. FIG. 1 illustrates one embodiment of the micropackaged device 100 of the present invention. In certain aspects, the micropackaged device 100 comprises a substrate for securing a device 110. A wide variety of devices can be packaged according to the present invention. Suitable devices include, but are not limited to, an integrated circuit (IC) chip, a printed circuit board (PCB), a microelectromechanical system (MEMS), a capacitor, an inductor, an oscillator, or a combination thereof. The devices to be protected can be a wired or a wireless PCB, thin-film integrated device, and the like. If the component or device is wireless (e.g., with a coil), the entire device can be totally encapsulated in the enclosure. Small electronic components can be mounted on a printed circuit board, which minimizes the amount of space necessary for the implant. FIG. 1 shows the device to include a combination of a PCB 105 and a thin-film integrated device 112.

The micropackaged device 100 comprises a corrosion barrier 120 (above and below the substrate) an daffixed to the substrate. The corrosion barrier is preferably made from a low-permeation material. Suitable low-permeation materials include, but are not limited to, glass, metal, ceramic, parylene, PET, PVC or a combination thereof. In certain preferred aspects, the corrosion barrier is made from glass or a metal such as a metal film. The substrate may have any number of designs including recesses and/or pockets for mounting electronic components and devices. As the number of devices and components will vary, so too will the number of recesses and pockets, each of which can have a different dimension. In some embodiments of the present invention, there may be an inner filler material to protect components and to provide impact strength.

In certain aspects, the corrosion barrier is affixed to the substrate with an adhesive. For example, the adhesive can be a low permeation adhesive. Suitable adhesives include, but are not limited to, epoxy, silicone, polyimide or a combination thereof.

In certain embodiments, the micropackaged device 100 of the present invention comprises optionally at least one feedthrough 133, 165 (shown as dashed lines to indicate that they are optional) disposed in the substrate to permit at least one input and/or at least one output line into the encapsulated micropackaged device. For example, if the device is wired, a cable can exit the encapsulation to make an external connection. The substrate can be integrated into the device or can be a separate component.

In certain aspects, the micropackage optionally contains at least one hermetic feedthrough 133 or 165 disposed in either the substrate, or bottom of the micropackage housing. In the embodiment shown in FIG. 1, two elongate hermetic feedthroughs 133, 165 are disposed in apertures of the micropackage 100. Such feedthroughs 133, 165 are each configured to permit an input/output line to infiltrate the hermetic enclosure or housing without degrading the hermeticity of the enclosure. Input/output lines may be, for example, wires (metal, copper, fiber optic, etc.), cables, tubes, and the like that facilitate the transfer of energy, data, or power between functional components and other implantable devices, external components, and the like.

In certain aspects, the feedthroughs enable the production of thinner or more compact implantable components as the device can be spread over larger surface areas. A "feedthrough" can include an electrically conductive path extending through an insulator (or insulative member). In some embodiments, the electrically conductive path electrically connects the functional components located in the interior of the encapsulated housing or sealed enclosure (i.e., a hermetically sealed, housing, and the like) of the micropackage to functional components external to the hermetic enclosure. That is, in some embodiments, the conductor provides an electrically conductive path from one side of the insulator in the enclosure to another side of the insulator outside the enclosure.

In certain aspects, the micropackaged device 100 of the present invention includes an encapsulation material layer of silicone 125 and a second encapsulation material layer of parylene 135 configured to encapsulate the micropackaged device. In certain aspects, the encapsulation material layer is a low-permeation material. For example, the low permeation material layer can be parylene, metal, silicone, ceramic, SU-8, polyimide, polyurethane, evaporated metal, epoxy, titanium or a combination thereof.

In certain instances, the encapsulation material layer(s) can be parylene. Although parylene-C is one preferred encapsulation material, other parylenes such as parylene N, C, D, HT, AM, A or combinations thereof can also be used. A skilled artisan will appreciate that the encapsulation material can be made of other materials as well. In certain aspects, the encapsulation material layer is a plurality of encapsulation material layers, such as at least two, 3, 4, 5, 6, 7, 8, 9 or even more encapsulation material layers. Each layer can be the same or different. In certain aspects, the encapsulation material layer defines a housing or enclosure. In certain aspects, the housing encapsulates a device. In certain instances, a device is disposed on a substrate or the substrate can be integrated into the device. In one particularly preferred embodiment, the encapsulation material layer is made of silicone and/or parylene.

In certain aspects, the encapsulation material layer comprises a plurality of encapsulation material layers. In one aspect, the encapsulation material layer creates an enclosed housing hermetically sealing the device and/or substrate and a corrosion barrier.

In one aspect, the corrosion barrier is coextensive with the interior of the enclosed housing. Alternatively, the corrosion barrier is coextensive with about 10% to about 90% such as 20% to about 60% or even about 50% of the total area of the interior of enclosed housing or an area commensurate with the device. In other aspects, the corrosion barrier is coextensive with about 5, 10, 20, 30, 40, 50, 60, 70, 80, 90 or about 99% of the interior area of the enclosed housing.

In one aspect, the corrosion barrier protects a metal pad(s) or the electronics of the device. The corrosion barrier can be attached to a device by an adhesive with an adhesion promoter.

In certain aspects, the micropackaged device of the present invention is an implantable prosthesis, such as a totally implantable prosthesis that can be temporarily or permanently implanted. The enclosure can be hermetically sealed to secure against the entry of water, water vapor and foreign bodies in order to maintain the proper functioning and reliability of the contents therein.

Communication with such an implanted prosthesis can be performed using either percutaneous connectors or wireless communication methods. An advantage of a wireless communication method over a percutaneous connector is the elimination of issues relating to possible infection or irritation related to devices that perforate the skin. Some of the kinds of signals that are communicated between an implanted prosthesis and an external device include power signals and data signals. Power signals can include signals that provide power from an external power supply to an implanted prosthesis, so that for example, a battery or electronic device present in the implanted prosthesis can be maintained in a suitable state of charge, or so that for example, a battery can be eliminated from the implanted prosthesis.

In one aspect of the present invention, there is provided a protective packaging for a long lifetime for a retinal implant in a mammalian subject such as a human being. In certain aspects, the use of an encapsulating coating together with a corrosion barrier layer is used to protect the implant device. In certain aspects, a thin film substrate architecture as disclosed in U.S. patent application Ser. No. 13/830,272, filed Mar. 14, 2013 and incorporated herein by reference is used along with an encapuslation material layer and a corrosion barrier.

Figure 2B:
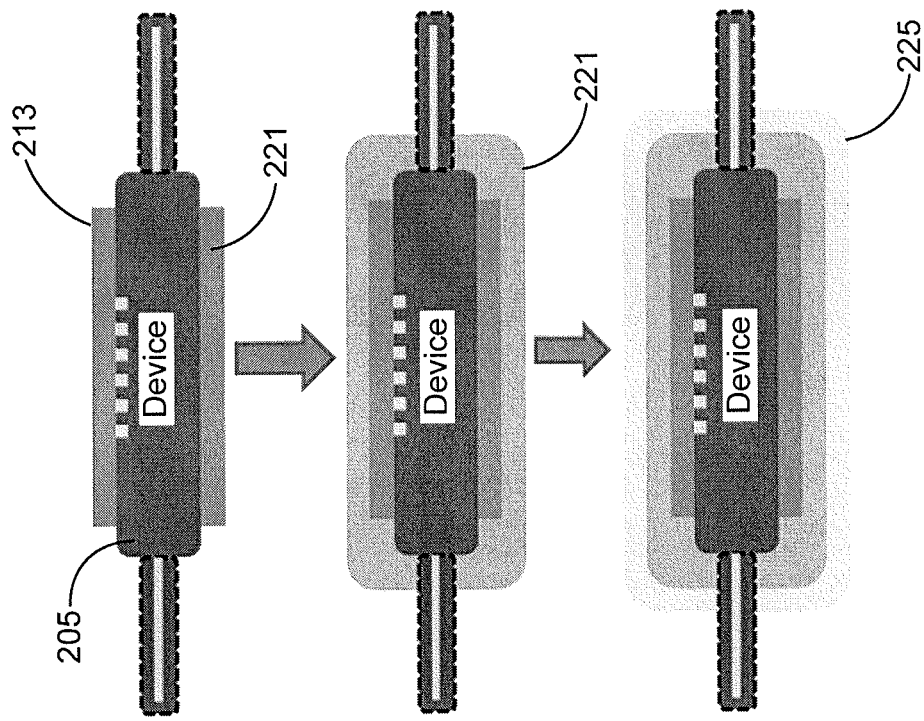
FIGS. 2A-B show (A) one embodiment of an exploded view of a micropackaged device of the present invention; (B) layers of the one embodiment of a micropackaged device of the present invention
Figure 2A:
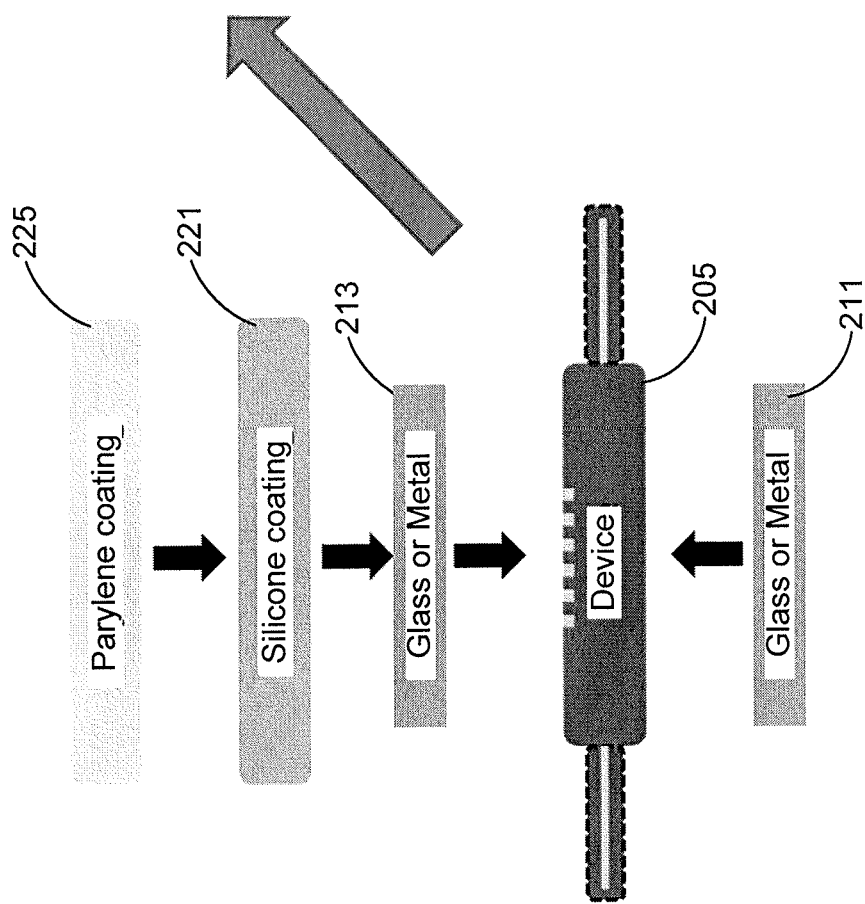

Turning now to FIG. 2A, the device to be packaged is covered with a corrosion barrier (213, 211) such as glass or metal (for example, above and below the device). The corrosion barrier e.g., a metal film, typically has good flexibility and can shield the electronics' of the device or the device per se. In certain aspects, the corrosion barrier protects the side where the electronics reside, or where a metal pad(s) is exposed. However, as more of the sides of the device are covered, the better the protection. In one aspect, after the corrosion barrier is attached, an adhesion promoter is applied, dip coated in silicone 221, and then followed by a parylene coating 225.

FIG. 2B illustrate one embodiment of the method of micropacking a device of the present invention. As shown therein, corrosion barriers 211, 213 are placed or disposed on both sides (top, bottom, left, right, or totally surround and the like) of the device 205 prior to encapsulating the device. Silicone 221 is added as a first encapsulation material layer. The second encapsulation material layer 225 is parylene. The outer protection or encapsulation layers of silicone 221 and parylene 224 can be further modified to have a better effect. Advantageously, the corrosion barrier and attachment changes the failure mode from fast diffusion to a slow undercut. In certain aspects, this extends the lifetime of a device.

Figure 3A:
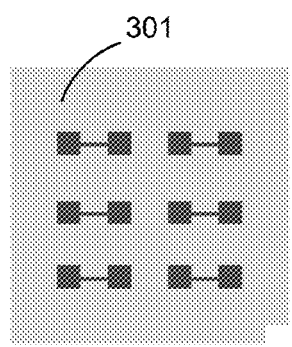
FIGS. 3A-D shows (A) shows a high-density multi-channel dummy resistor chips; (B) shows a corresponding parylene flex, which is also designed and fabricated to integrate with the dummy resistor chips; After alignment, (C) shows the electrical connection of this structure is done by a conductive epoxy squeegee technique; and (D) shows that the overall resistance of each device is measured to be around 40Ω.
Figure 3B:
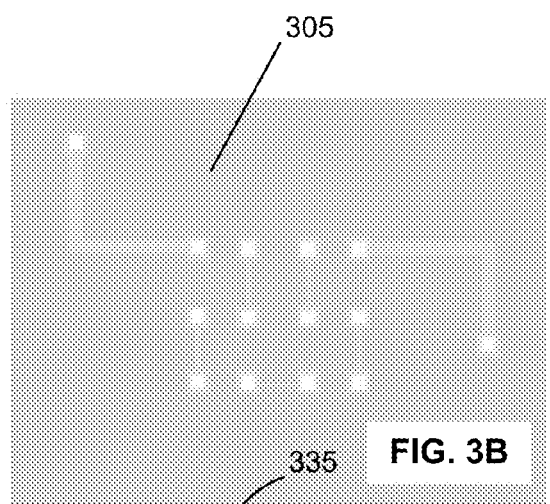
Figure 3C:
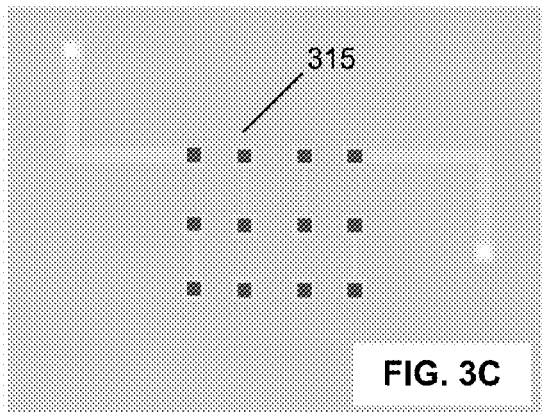
Figure 3D:
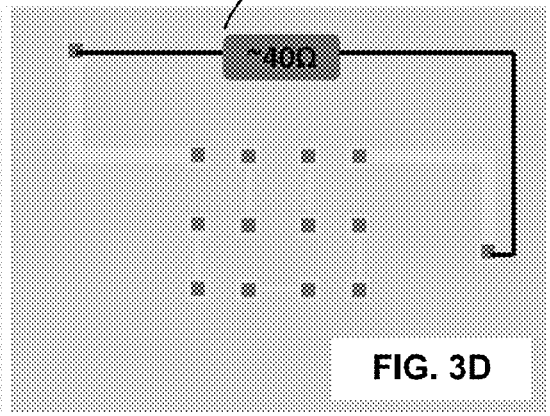

FIGS. 3A-D show embodiments of a high-density, multi-channel resistor chip used to simulate a high lead count ASIC chips. In one aspect, these resistor chips are then integrated with the parylene flex by a conductive epoxy squeegee technique, finished with a corrosion barrier (e.g., glass) and an encapsulating packaging scheme of the present invention. To test the chip, it can be actively soaked in a saline solution until failure is detected. In certain aspects, the failure can be defined as 50% change in line resistance. More specifically, FIG. 3A shows a high-density multi-channel dummy resistor chips 301. FIG. 3B shows a corresponding parylene flex 305, which is also designed and fabricated to integrate with the dummy resistor chips. After alignment (FIG. 3C), the electrical connection of this structure 315 is done by a conductive epoxy squeegee technique as the tested devices, and the overall resistance of each device is measured to be around 40Ω 335 (see, FIG. 3D).

In certain aspects, the micropackaged device utilizes materials with approximately a zero water vapor transmission rate (WVTR), such as glass, or metal (metal film), on an electronic device to protect the electronics inside. In this manner, the water vapor cannot diffuse through this material to corrode the device. In fact, one way for water or a biological fluid to diffuse inside is to attack the interface between the glass and parylene flex. After inclusion of a corrosion barrier (e.g. glass), additional encapsulation layers such as an adhesive, or parylene layers are applied to further protect the device.

Figures 4A, 4B:
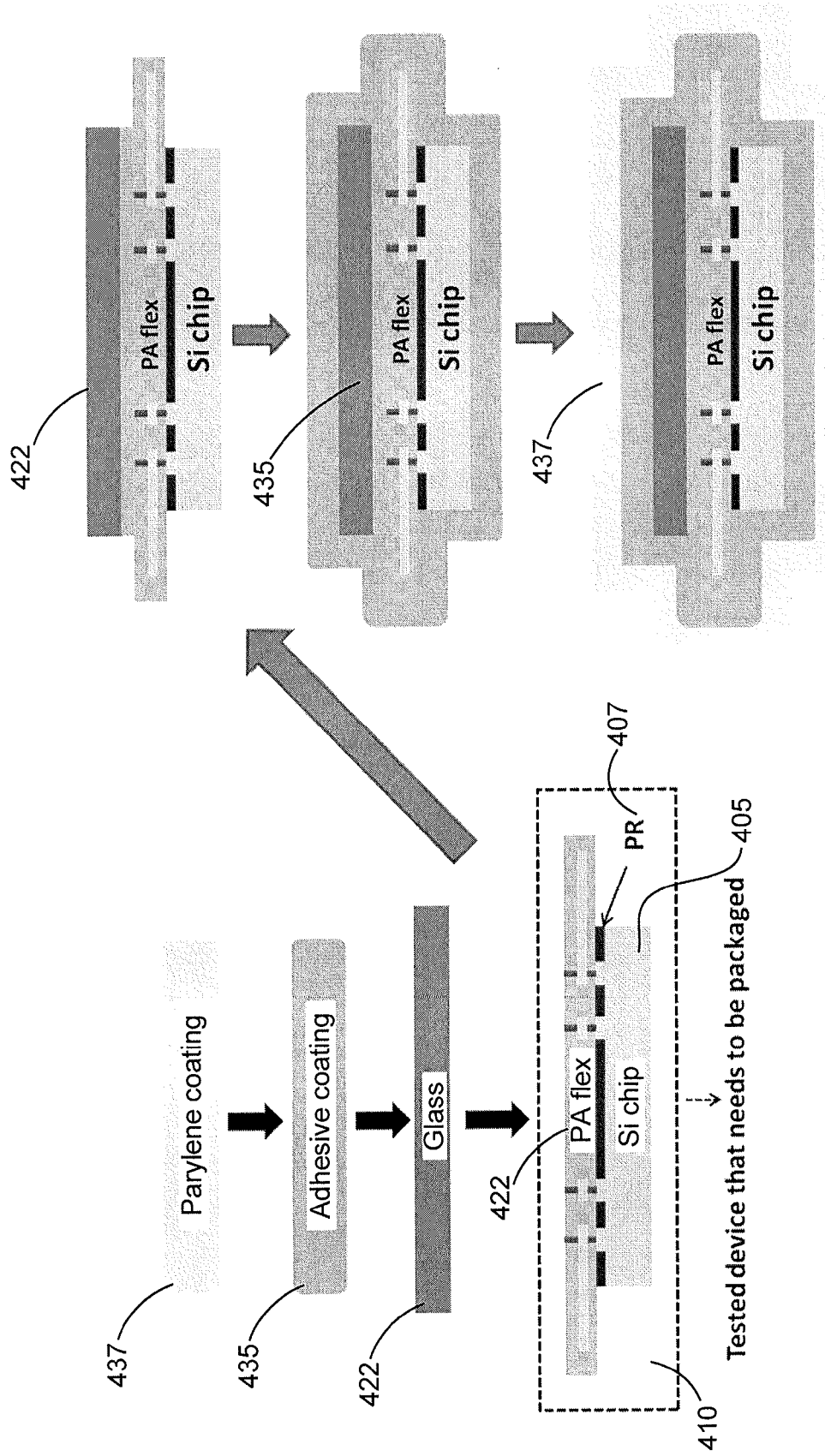
FIGS. 4A-B shows one embodiment of a micropackaged device of the present invention.

FIGS. 4A-B show one embodiment of a method of micropackaging a device of the present invention. FIG. 4A shows a test device 410 prior to being packaged. The device 410 has a silicon substrate 405 with photoresist 407 and parylene flex 411. The corrosion barrier 422 of glass is used and thereafter an adhesive layer 435 is used to encapsulate the device. A parylene layer 437 can cover over (overlay or encapsulate) the adhesive layer. FIG. 4B shows the corrosion barrier 422, a first encapsulation layer made of adhesive 435 and then a second encapsulation layer made of parylene 437.

In certain instances, the second encapsulation layer or outermost shell can be designed to have a desired impact resistance. For example, if the implant is designed to be beneath a subject's skin, the device may be subjected to external forces due to its proximity to the outside environment. In these instances, additional encapsulation layers may be required or stronger materials can be used.

In another embodiment, the present invention provides a method for micropackaging a device, the method comprising: providing a substrate for securing a device; affixing a corrosion barrier to the substrate; optionally providing at least one feedthrough disposed in the substrate to permit at least one input and or at least one output line into the micropackaged device; and encapsulating the micropackaged device.

Figure 5:
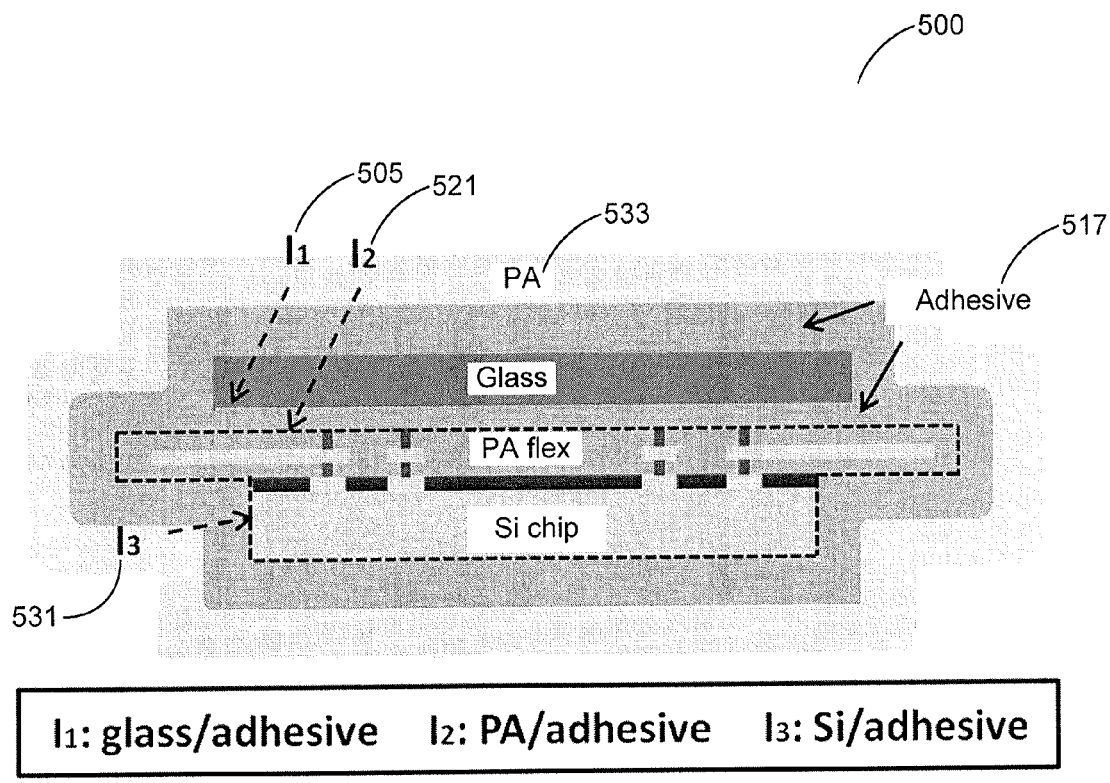
FIG. 5 shows one embodiment of a micropackaged device with three different interfaces of materials in the structure.

FIG. 5 shows one embodiment of a micropackaged device 500 of the present invention. In this particular embodiment, there are three different interfaces of materials in the structure. Interface 1 is a glass to adhesive 505 interface; Interface 2 is parylene to adhesive 521 interface; and Interface 3 is silicon to adhesive 531 interface. Suitable adhesives include, but are not limited to, bio-compatible silicone and/or epoxy. In certain instances, a silicone adhesion promoter (SAP) is used to further enhance the adhesion. In certain aspects, a first encapsulation material layer is an adhesive 517 and then a second encapsulation material layer of parylene 533 is used to encapsulate the entire device. Securing these interfaces of the micropackaging are aspects of the present invention.

In prior implant devices, it is known that electrochemical corrosion is one main failure mechanism. Therefore, water (vapor) diffusion through the protecting barrier and the resulting corrosion on conductive epoxy and/or electrode metal pads are significant issues. Although a thicker barrier can be adopted to extend the device lifetime, the size enlargement, the device stiffness and the heat dissipation become resulting concomitant problems. The inventive packaging scheme with a corrosion barrier has overcome these limitations. The nature of low water vapor transmission rate (WVTR) and high thermal conduction, of for example, glass (i.e., compared to normal polymers) makes this structure and corrosion (e.g., moisture) barrier very useful.

FIG. 5 shows that additional biocompatible adhesives and parylene coating can be used in handling protection. In certain embodiments, various experiments were performed to determine which adhesive and/or adhesion promoter can be used to create a long-lasting interface. In fact, in certain other aspects, the present invention provides suitable adhesives and interface treatments for the various interfaces of the micropackaged device architecture (e.g., the three different interfaces (I-1, I-2, and I-3). The present invention provides strong interfaces to block water vapor and concomitant corrosion.

FIGS. 6A-D show certain of the interfaces in the micropackaging schemes of the present invention. In one aspect, a biocompatible epoxy such as M-121HP or a biocompatible silicone such as MED-6219 can be used. In certain aspects, the adhesive robustness of an epoxy and a silicone on different substrates were investigated. For example, an epoxy and a silicone on silicon, glass, and parylene substrates with and without interface treatment of a silicone adhesion promoter (e.g., MED-160) was investigated. The test micropackaged devices were made and tested. The samples were soaked in a high temperature (e.g., 97° C.) saline solution to compare the undercut rates. As used herein, the term "undercut" is used to describe the lift-off rate of the adhesive at the interface of the adhesive and the substrate surface. FIG. 6A illustrates a silicon/adhesive interface. FIG. 6B illustrates a glass/adhesive interface. FIG. 6C illustrates a parylene/adhesive interface. FIG. 6D shows this undercut location 602, 610 and the lift off rate at the interface.

In certain aspects, accelerated soaking tests show that a biocompatible silicone (e.g., MED-6219) with a silicone adhesion promoter (e.g., MED-160) has the lowest undercut rate on all the materials tested. Thus, silicone is one preferred adhesive as shown in FIG. 7A-C.

Figures 7A, 7B, 7C:
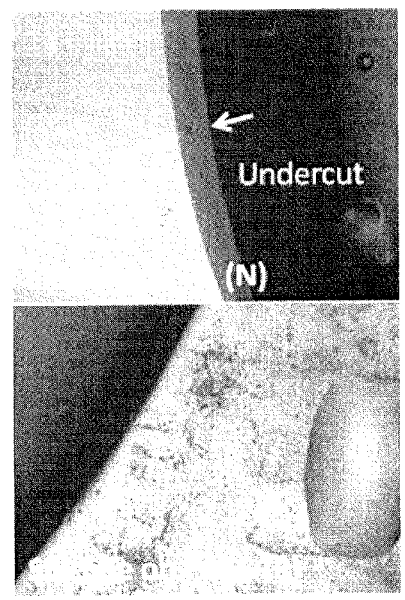
FIGS. 7A-C show (A) tabulated data; (B) shows an aspect of silicone on parylene substrate without SAP; (C) shows silicone on parylene substrate with silicone adhesion promoter (SAP).

FIG. 7B shows that there is an undercut for silicone on a parylene substrate if silicone adhesion promoter (SAP) is not used. However, FIG. 7C shows that with a silicone adhesion promoter (SAP), there is almost no undercut for silicone on a parylene substrate. The table in FIG. 7A shows that with SAP, the undercut was greatly decreased for both epoxy and silicone with all substrates. In addition, silicone is more flexible than epoxy. Thus, the testing results show that, with a silicone adhesion promoter, both biocompatible epoxy and biocompatible silicone have much slower undercut rates on different substrates. According to the data, silicone has slower undercut rates compared to epoxy. Moreover, silicone is more flexible and hydrophobic. As such, in certain aspects, silicone was selected as the adhesive to apply on these interfaces.

Quite advantageously, with a corrosion barrier (such as glass) and encapsulated micropackaging scheme, the lifetime of various implantable devices and components can be extended to more than 10 years. In certain instances, the size of the resistor chip is designed to be approximately 6 mm by 6 mm, while the corrosion barrier (e.g., glass) used is about 10 mm by 10 mm, so there is only 2 mm of undercut limit on each side, which translates to around 5 years/mm of life time design. In other instances, the time for body fluid to undercut along the interface between the corrosion barrier and parylene flex can be extended. For example, if the undercut length is increased to 3 mm, the lifetime of a device can be extended to around 15 years. Accordingly, longer lifetime can be designed with longer undercut length.

Figure 8B:
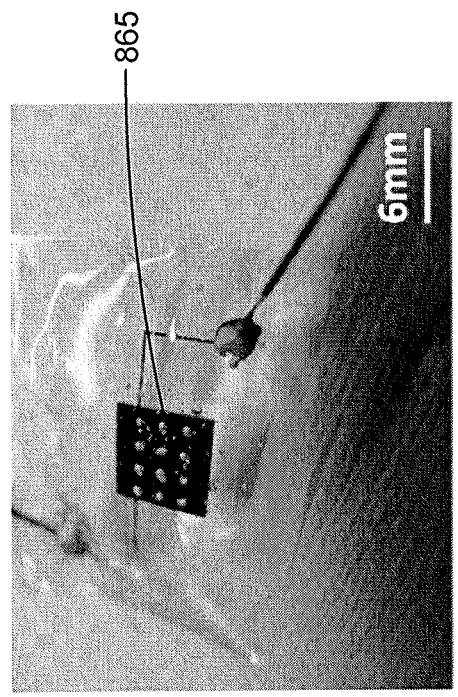
FIGS. 8A-B show (A) a corresponding parylene devices; and (B) integration of them together as the testing samples.
Figure 8A:
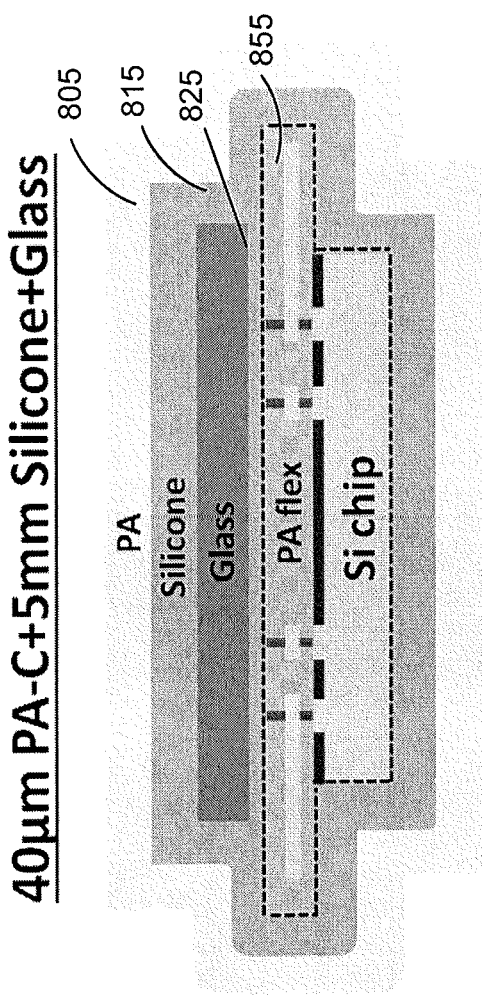

FIGS. 8A-B show the corresponding micropackaging devices and integration of them together as the testing samples. As shown in FIG. 8A, parylene 805 is an encapsulating material layer. In addition, silicone 815 is an encapsulating material layer. In this particular embodiment, glass 825 is used as a corrosion barrier to the device 855. FIG. 8B is a picture of a real micopackaging scheme with a device 865.

The inventive micropackaged device was tested. Testing results of the implantable devices of the present invention indicate that humidity is one reason of failure after implantation. Thus, the water vapor transmission rate ("WVTR") is an accurate parameter to quantify the effectiveness of the encapsulated micropackaged device, which advantageously comprises a corrosion barrier.

FIG. 9A shows a testing sample with glass-encapsulated packaging under an active soaking test. FIG. 9A shows the device with a glass-protected packaging in saline 915, after the power supply 905 is connected, the water vapor can gradually diffuse through the thick protection barrier. However, it cannot attack the parylene device directly 935. The observed failure mode is found to be a very slow undercut 925 along the interface between the glass and silicone adhesive, as shown. FIG. 9B shows slow undercut 955 along the interface is a potential cause for failure.

Figure 10:
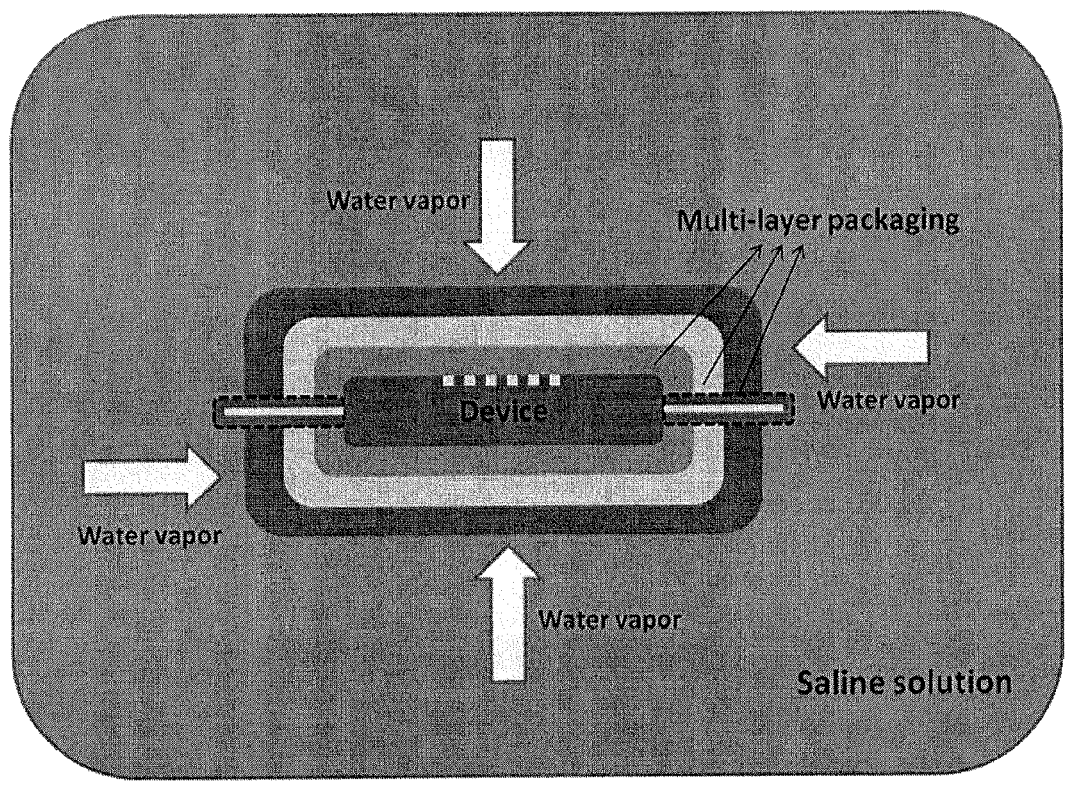
FIG. 10 shows one embodiment of a micropackaged device of the present invention in saline.
Figures 11A, 11B:
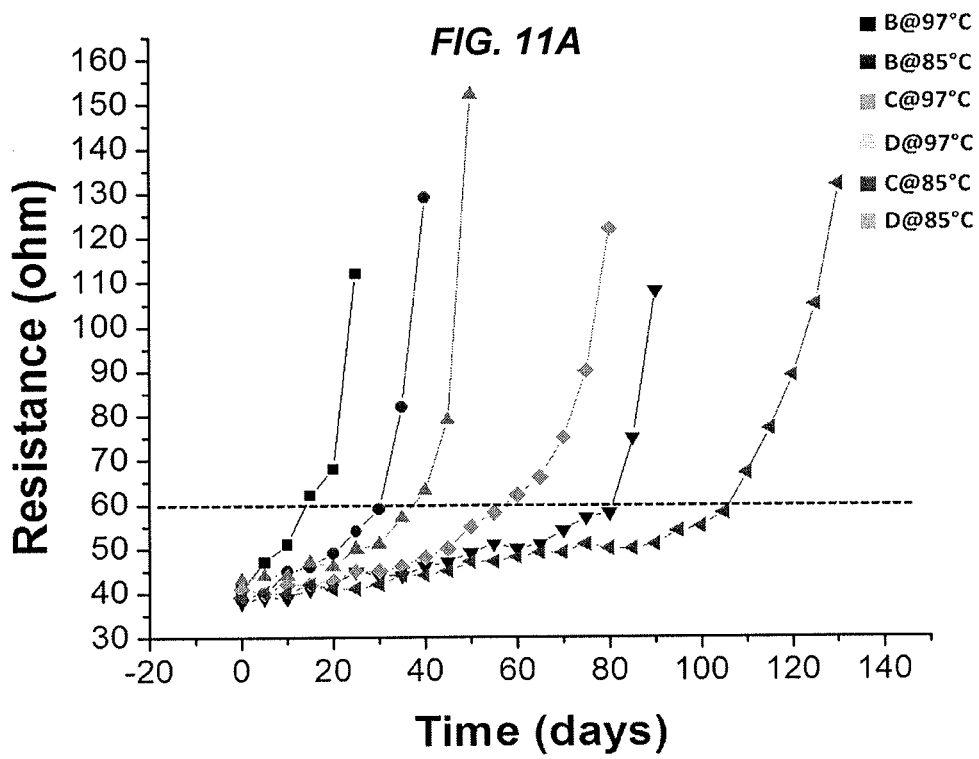
FIGS. 11A-B show (A) a graph of resistance (y-axis) versus days (x-axis) and (B) a tabulation of the mean time to failure (MTTF).

FIG. 10 shows the device with a multilayer packaging in saline. FIG. 11A-B quantitates the various architectures and the life-time of the protection scheme. FIG. 11A is a graph of resistance (y-axis) versus days (x-axis). The mean time to failure (MTTF) can be calculated using an approximated Arrhenius relationship (see, J. H. Chang, B. Lu, Y. C. Tai, *Digest Tech. Papers Transducers '11 Conference*, Peking, Jun. 5-9, 2011, pp. 378-381) at body temperature and is expressed as:

$$MTTF \sim A\exp\left(-\frac{Ea}{kT}\right) \quad (1)$$

Where A is the pre-exponential constant; Ea (eV) is the activation energy; and k is the Boltzmann's constant. The failure modes are based on the serious corrosion of metal pads and conductive epoxy. Protection scheme A (no protection); B is 40 μm of parylene; C is 5 mm of silicone and 40 μm of parylene; and D is 40 m of parylene, 5 mm of silicone and a glass corrosion barrier. Protection scheme D has a MTTF of 10.3 years (see, FIG. 11B).

FIGS. 12A-B show one embodiment of a device suitable to be micropackaged using the present invention. In this instance, the present invention provides a retinal implant. In certain aspects, the present invention provides a wireless retinal implant 1200 having a high density multi-channel IC chip, discrete components (caps, inductors, oscillators, and the like), and coils (power and data coils) packaged with a high-density stimulating electrode array. FIG. 12A shows the schematic of a retinal implant chip 1205 having discrete components 1230 and in electrical communication 1207 with output electronics 1210. The chip also has a data coil 1220 and a power coil 122.

As shown in FIG. 12B, the wireless retinal prosthesis is implanted in a mammalian eye 1240. The chip 1205 and associated components are implanted in the front of the eye (proximal part of the eye) with a cable 1242 leading to the output electrodes 1210 with an electrode array 1270 implanted in the distal area of the eye. A shown in FIG. 12B, the intraocular RF coil 1245 and the integrated ASICs 1260 are implanted in the front of the eye.

In one aspect, the device to be micropackaged is an integrated circuit (IC) chip. The micropackaged device comprises a substrate such as a thin-film substrate e.g., a parylene substrate.

In certain instances, the substrate has a first thin-film layer; a metal adjacent to the first thin-film layer; and a second thin-film layer adjacent to the metal to form a thin-film metal thin-film sandwich. The first thin-film layer and the second thin-film layer are each independently selected from the group of parylene, polyimide, Teflon, Kapton, or a printed circuit board (PCB). In certain aspects, the first thin-film layer and the second thin-film layer are each parylene. In certain aspects, the device is integrated in the substrate by a conductive epoxy squeegee electrical connection.

In certain aspects, the device is integrated into a substrate by a photo-patternable adhesive used as mechanical glue. The photo-patternable adhesive or epoxy is photoresist such as SU-8, AZ4620, AZ1518, AZ4400, AZ9260, THB-126N, WPR-5100, BCB, polyimide, or a combination thereof. Those of skill in the art will know of other photoresist materials suitable for the present invention. In certain aspects, the parylene substrate is first treated with oxygen plasma to enhancing bonding.

In certain aspects, the present invention provides a fabrication process 1300 for a parylene-substrate, such as a flexible parylene-C substrate. In one exemplary embodiment, FIG. 13A shows a 5 μm first parylene-C layer (bottom layer) 1320 deposited on a silicon wafer substrate 1310 such as a HMDS treated silicon wafer, which aids in the device being detached such as being released in distilled or deionized water, preferably deionized water.

Next, as is shown in FIG. 13B, adjacent to the first parylene layer 1320 (bottom parylene layer) is a metal 1330 such as a titanium/gold (Ti/Au) alloy for a metal lift-off. The metal provides an electrical connection. A second parylene layer 1350 (top layer) such as a thicker parylene-C (about 40 μm) layer is then deposited to complete the parylene-metal-parylene sandwich structure as is shown in FIG. 13C. The process includes providing a mask 1360 such as a metal mask (e.g., aluminum) deposited as a parylene-C etching mask to etch through the thick parylene-C layer as is shown in FIG. 13D. The metal mask can be about 0.1 to about 0.3 μm in thickness.

In certain instances, as is shown in 13E photoresist 1365 can be used to pattern the metal. In certain embodiments, the sacrificial layer is about 0.5 to about 2 μm thick such as about 1 μm thick or about 0.1 to about 0.3 μm in thickness. The sacrificial layer is preferably patterned using photolithography. Suitable materials for the photoresist layer include, but are not limited to, SU-8, AZ4620, AZ1518, AZ4400, AZ9260, THB-126N, WPR-5100, BCB, polyimide, or a combination thereof.

In certain instances, as is shown in 13F, the photoresist can be patterned 1370. Thereafter, the metal (e.g., aluminum) is patterned as is shown in 13G. The photoresist is thereafter removed (FIG. 13H). Electrode sites 1372, 1375 and device contour 1380 are defined by reactive ion etching (such as a 2-step $O_2$ plasma etching as is shown in FIG. 13I) or deep reactive ion etching (DRIE) can be used. The device is release from the wafer as is shown in FIG. 13J.

Although the foregoing example uses parylene-C, the processes and embodiments of the device herein are not so limited. Other parylenes such as parylene N, C, D, HT, AM, A or combinations thereof can also be used. Parylene-C is the preferred parylene. Although parylene is the preferred substrate, a skilled artisan will appreciate that the material can be other thin-film polymers such as polyimide, Teflon, Kapton, or a printed circuit board (PCB) and the like.

Other materials useful for substrate and/or carrier design include, but are not limited to, silicon, glass, steel, G10-FR4, or any other FR4 family epoxy, etc. In some embodiments, the silicon substrate is used only as a carrier during fabrication and is accordingly removed before the package is complete. In other embodiments, the carrier remains an integral part of the package.

In certain aspects, the silicon-wafer used in the methods is treated with 1,1,1,3,3,3-hexamethyldisilazane (HMDS). A skilled artisan will appreciate other treatments can be used to release the parylene structure from the silicon wafer.

In certain aspects, the first parylene layer 1320 and the second parylene layer 1350 are deposited on a silicon substrate by chemical vapor deposition (CVD). The first layer has a thickness of between about 0.1 μm to about 100 μm thick such as 10, 20, 30, 40, 50, 60, 70, 80, 90, or 100 μm. Preferably, the thickness of the first parylene layer (bottom layer) is between about 1 μm and about 10 μm thick such as about 1, 2, 3, 4, 5, 6, 7, 8, 9, or 10 μm thick.

Typically the second parylene layer (top layer) 1350 is thicker than the first parylene layer 1320. In one instance, the second parylene layer is between 10 μm and 200 μm thick such as 10, 20, 30, 40, 50, 60, 70, 80, 90, 100, 110, 120, 130, 140, 150, 160, 170, 180, 190 or 200 or even thicker. Preferably, the second parylene layer is between 20 μm and 60 μm thick such as about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 μm thick.

In certain aspects, the metal 1330 used for the lift-off is a titanium/gold (Ti/Au) alloy. However, other suitable metals and alloys include, but are not limited to, Cr/Au, Ni/Au, Ti/Au, Al/Ti, Ag/Ti, Cr/Au/Ti/Ni/Au, Ni/Pd/Au, Ti/Ni/Au or combinations thereof. Those of skill in the art will know of other metals useful for the present invention.

The process includes providing a mask such as a metal mask deposited as a parylene-C etching mask to etch through the second parylene-C layer. In general, etching is a reactive ion etching (RIE) masked by a metal mask. In addition, deep reactive etching can be used (DRIE). Other suitable mask materials are also useful. The RIE can be oxygen plasma etching.

A skilled artisan will appreciate that the parylene layers of the parylene devices described herein are not limited to two parylene layers. In addition, the metal of the parylene device is not limited to a single metal. The parylene devices are based on a sandwich structure. As long as a metal is sandwiched by a top and a bottom parylene layer, there can be numerous layers stacked on the substrate. In addition, there can be a plurality of masks to open the electrodes and define the contour of the device(s).

In certain instances, the process described is used to generate multiple parylene-metal-parylene sandwich layers on a carrier (e.g., a silicon wafer) such as a plurality of sandwich layers including 2, 3, 4, 5, 6, 7, 8, 9, 10 or more parylene-metal-parylene sandwich layers. Although the process just described generates 1 sandwich layer, a skilled artisan will appreciate that the process can be repeated to make any number of sandwich layers.

In certain aspects, the inventive thin-film (e.g., parylene) substrate hosts electronic components such as application specific integrated circuits (ASICs), which are interconnected via metallization traces, such as about 3.7 µm wide metallization trace. In one embodiment, the fabricated flexible parylene-C substrate is connected with an IC chip and other discrete components. In certain other aspects, the substrate or micro-module of the present invention contains a variety of components including, but not limited to, one or more integrated circuits, ASICs, interconnect layers, heat sinks, conductive vias, passive devices, MEMS devices, sensors, pre-manufactured electrical components, transistors, resistors, capacitors, inductors, micropumps and filters. The components are arranged and stacked within the module in a wide variety of different ways. The layers and components of the module can be deposited and processed using various conventional wafer level processing techniques, such as spin coating, lithography and/or electroplating.

The parylene package can include many other types of devices and components than the ones illustrated. The package can also contain almost any number of active and/or passive devices. Examples of such active and/or passive devices includes resistors, capacitors, oscillators, magnetic cores, MEMS devices, sensors, cells, communication devices, integrated thin film battery structures, inductors, and the like. These devices can be positioned and/or stacked in various locations within the package. The components may take the form of prefabricated discrete components or may be formed in-situ. One advantage of the lithography-based process used to create the present package is that these and other components can be formed in-situ during the layered formation of the package. That is, while prefabricated, discrete components can be placed in almost any position within package, components can also be fabricated directly onto any photo-imageable layer using any suitable technique, such as conventional sputtering and/or electroplating.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A micropackaged device, said micropackaged device comprising:
    a device;
    a thin-film substrate for securing said device, said thin-film substrate comprising:
    a first thin-film parylene layer, which is 1-10 µm thick;
    a metal adjacent to the first thin-film parylene layer;
    a second thin-film parylene layer, which is 20-60 µm thick, and which is adjacent to the metal to form a thin-film metal thin-film sandwich, wherein said second layer of thin-film has an opening, said opening having at least one electrical contact provided on an internal surface thereof, said opening configured to accept at least one electrical circuit device and to provide electrical communication between said at least one electrical contact and said at least one electrical circuit device;
    a corrosion barrier affixed to said substrate with an adhesive, wherein the corrosion barrier is made of a metal, ceramic or glass, which is disposed above and below the device;
    at least one feedthrough disposed in said substrate to permit at least one input and or at least one output line into said micropackaged device; and
    an encapsulation material layer made of parylene, silicone or a combination thereof configured to encapsulate said micropackaged device, wherein said encapsulation material layer creates an enclosed housing, wherein the corrosion barrier is 30% to 99% of the total area of the interior of enclosed housing, hermetically sealing said substrate and said corrosion barrier.

2. The micropackaged device of claim 1, wherein said device is a member selected from the group consisting of an integrated circuit (IC) chip, a printed circuit board (PCB), a microelectromechanical system (MEMS), a capacitor, an inductor, an oscillator, and a combination thereof.

3. The micropackaged device of claim 1, wherein said corrosion barrier is a material selected from the group consisting of metal and ceramic.

4. The micropackaged device of claim 3, wherein said corrosion barrier is made from a metal.

5. The micropackaged device of claim 4, wherein said metal is a metal film.

6. The micropackaged device of claim 1, wherein said corrosion barrier is made from glass.

7. The micropackaged device of claim 1, wherein said adhesive is a low permeation adhesive.

8. The micropackaged device of claim 1, wherein said adhesive is a member selected from the group consisting of an epoxy, silicone and polyimide.

9. The micropackaged device of claim 1, wherein said encapsulation material layer is parylene.

10. The micropackaged device of claim 1, wherein said encapsulation material layer is silicone.

11. The micropackaged device of claim 1, wherein said encapsulation material layer comprises a plurality of encapsulation material layers.

12. The micropackaged device of claim 1, wherein the corrosion barrier is coextensive with about 30% to about 60% of the total area of the interior of enclosed housing.

13. The micropackaged device of claim 1, wherein said micropackaged device is an epiretinal implant integrated device.

14. The micropackaged device of claim 1, wherein the thin-film substrate extends from the enclosed housing to an outer surface.

15. The micropackaged device of claim 14, wherein the outer surface comprises an electrode array in electrical communication with the substrate.

16. The micropackaged device of claim 14, wherein the outer surface extends from the enclosed housing through the feedthrough.

17. The micropackaged device of claim 14, wherein the substrate extension to the outer surface is a made from a material selected from the group consisting of parylene, silicone, or a metal alloy.

18. The micropackaged device of claim 1, wherein the device having at least one electrical circuit is an integrated circuit (IC) chip.

19. The micropackaged device of claim 18, wherein the device is integrated in the substrate by a conductive epoxy squeegee electrical connection.

20. The micropackaged device of claim 18, wherein the device is integrated into the substrate by a photo-patternable adhesive used as a mechanical glue.

21. The micropackaged device of claim 20, wherein the photo-patternable adhesive or epoxy is photoresist.

22. The micropackaged device of claim 21, wherein the photoresist is a member selected from the group consisting of SU-8, AZ4620, AZ1518, AZ4400, AZ9260, THB-126N, WPR-5100, BCB, and polyimide.

23. The micropackaged device of claim 1, wherein the substrate is first treated with oxygen plasma to enhance bonding.

\* \* \* \* \*